United States Patent [19]

Chikama

[11] Patent Number: 5,345,926
[45] Date of Patent: Sep. 13, 1994

[54] MEDICAL OBSERVATION INSTRUMENT
[75] Inventor: Toshio Chikama, Tokyo, Japan
[73] Assignee: Kabushiki Kaisha Machida Seisakusho, Tokyo, Japan
[21] Appl. No.: 10,990
[22] Filed: Jan. 29, 1993
[30] Foreign Application Priority Data Feb. 10, 1992 [JP] Japan .................................. 4-057344

[51] Int. Cl.⁵ ................................................ A61B 1/22
[52] U.S. Cl. ........................................... 128/9; 128/11; 128/6
[58] Field of Search ........................... 128/3, 7, 9, 11

[56] References Cited

U.S. PATENT DOCUMENTS

| | | | |
|---|---|---|---|
| 2,896,611 | 7/1959 | Moore | 128/3 |
| 3,384,076 | 5/1968 | Speelman | 128/9 |
| 3,698,387 | 10/1972 | Moore et al. | 128/9 |
| 3,766,909 | 10/1973 | Ozbev | 128/11 |
| 4,685,452 | 8/1987 | Riester | 128/9 |

FOREIGN PATENT DOCUMENTS 46-27034  9/1971  Japan .

Primary Examiner—Richard J. Apley
Assistant Examiner—Beverly A. Meindl
Attorney, Agent, or Firm—Fish & Richardson

[57] ABSTRACT

A medical observation instrument has a body and an observation sleeve. The body has a grip portion, and a support portion disposed at a distal end of the grip portion. This support portion has a circular arcuate portion. The observation sleeve is made of a transparent material. The observation sleeve has a mount portion of a circular section received in and removably attached to the support portion of the body. A light emission member is received in a receiving hole formed in an inner peripheral surface of the support portion. An illumination light from the light emission member is emitted toward the mount portion of the observation sleeve, reflected by the inner peripheral surface of this mount portion, passed through a peripheral wall of a distal end portion of the observation sleeve while being reflected by inner and outer peripheral surfaces of the observation sleeve, and then output forwardly of a distal end face of the observation sleeve.

9 Claims, 5 Drawing Sheets

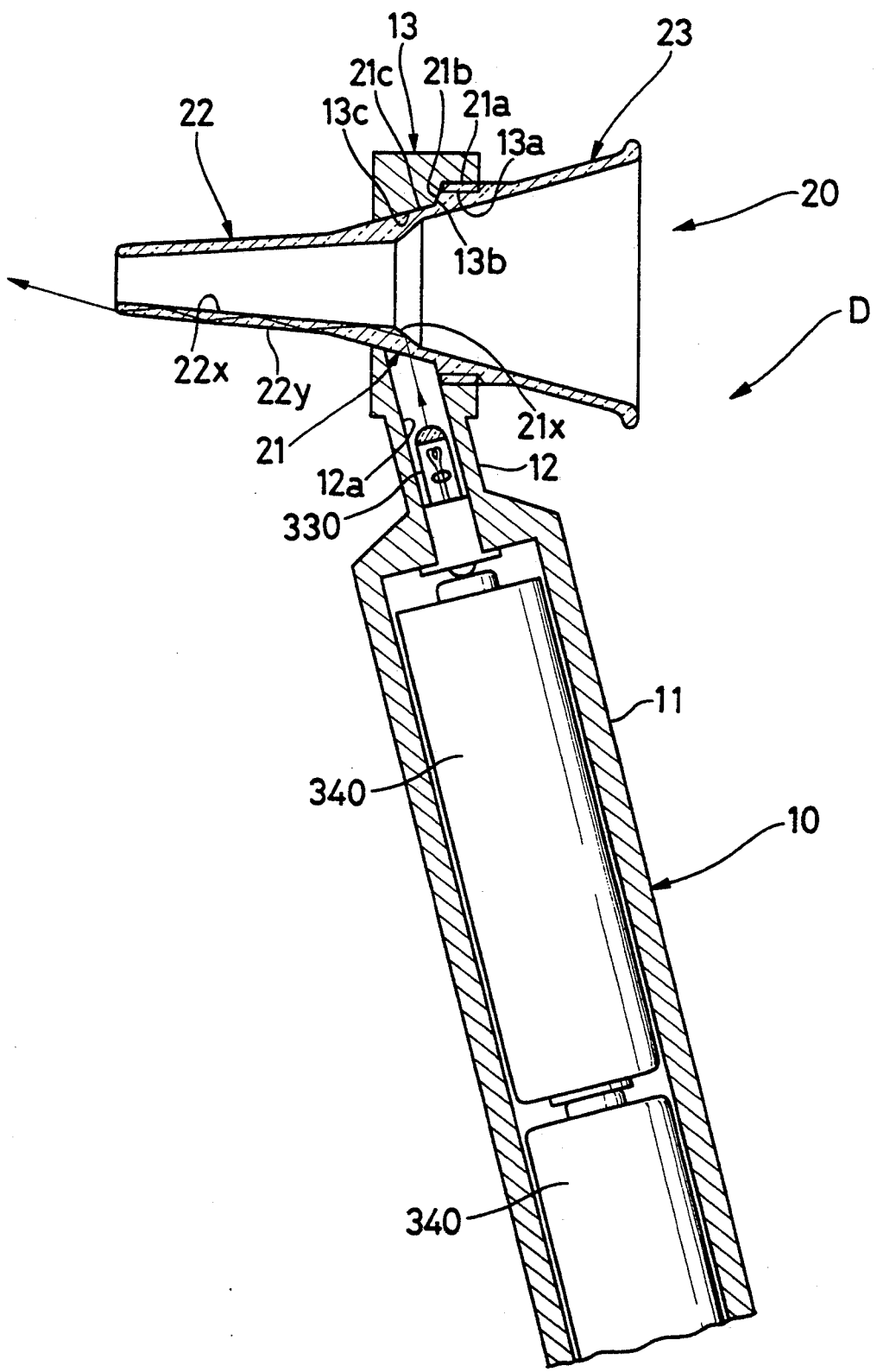

MEDICAL OBSERVATION INSTRUMENT

BACKGROUND OF THE INVENTION

This invention relates to a medical observation instrument such as an otoscope which is used for observing the ear canal.

As discussed in U.S. Pat. No. 3,698,387, an otoscope comprises an elongated grip member and an observation sleeve removably attached to a distal end of the grip member. The observation sleeve is inclined longitudinally of the grip member. A physician holds this grip member by the hand, and inserts the distal end portion of the observation sleeve into the ear canal for observation. A lug is formed on an outer periphery of the observation sleeve, and a distal end portion of a holding sleeve is attached to this lug by means of an adhesive. A basal end portion of the holding sleeve is removably connected to the distal end of the grip member. A lamp is mounted in the holding sleeve. Illumination light from this lamp is supplied to the ear canal through a bundle of optical fibers.

The optical fiber bundle extends axially of the observation sleeve and is embedded in a peripheral wall of the observation sleeve, one end of the bundle is located at an end face of the lug of the observation sleeve and the other end is located at a distal end face of the observation sleeve.

In the otoscope of the above U.S. pat. publication, since various instruments are inserted into the ear canal through the observation sleeve in medical treatment, the observation sleeve is easily soiled. Accordingly, it is desirable that the soiled observation sleeve be disposable, and a new observation sleeve is used for each patient. However, since the observation sleeve thus constructed is expensive because the optical fibers are embedded therein and the lamp and the holding sleeve are attached to the lug of the observation sleeve, the observation sleeve is disposable.

With reference to other related art, an instrument for observing an anus disclosed in FIG. 3 of Japanese Utility Model Publication No. Sho 46-27034 includes an observation sleeve made of a transparent material. A projection extending in an inclined direction relative to an axis of the observation sleeve is formed on an outer periphery of the observation sleeve and is integral with the observation sleeve. This projection is also transparent. One end of the projection is removably attached to a distal end portion of a grip member. One end of an optical fiber bundle is received in the grip member, and the other end is connected to a light source. Light from the light source is supplied to one end face of the projection via the optical fiber bundle, then passed through the interior of the projection from this end face, and then passed through a peripheral wall of the observation sleeve while being reflected by inner and outer peripheral surfaces of the observation sleeve, so as to reach a distal end of the observation sleeve. Since tiny irregularities are formed on an outer periphery of the distal end of the observation sleeve, most of the light is irradiated outside from the outer periphery of the distal end of the observation sleeve. In this Publication, it is described, in order to ensure reflection, that the surfaces of the observation sleeve may be metal plated.

In the instrument disclosed in the above Utility Model Publication No. Sho 46-27034, since the projection is formed at the distal end portion of the observation sleeve, the configuration of the observation sleeve becomes complicated and the manufacturing cost of the observation sleeve becomes high. As a result, the observation sleeve becomes unsuitable to be disposed. Furthermore, since the observation sleeve is supported by the grip member with a minute end portion of the projection inserted into the grip member, the support for the observation sleeve is unstable.

SUMMARY OF THE INVENTION

It is an object of the present invention to provide a medical observation instrument, in which an observation sleeve is disposable and in which the observation sleeve is supported in a stable manner.

According to the present invention, there is provided a medical observation instrument, comprising:

(a) a body including a grip portion and a support portion disposed at a distal end of the grip portion, the support portion having a circular arcuate portion, a receiving hole being formed in that portion of an inner peripheral surface of the circular arcuate portion corresponding to the grip portion;

(b) an observation sleeve removably attached to the body and extending in a direction intersecting a longitudinal direction of the grip portion of the body, the observation sleeve being made of a transparent material, the observation sleeve including a mount portion of a circular section received in and removably attached to the support portion of the body, and a distal end portion of a circular section extending forwardly of the mount portion; and (c) light emission means for supplying an illumination light to the observation sleeve, the light emission means being received in the receiving hole of the body, the illumination light from the light emission means being emitted toward the mount portion of the observation sleeve, reflected by an inner peripheral surface of the mount portion, passed through a peripheral wall of the distal end portion while being reflected by outer and inner peripheral surfaces of the distal end portion, and then outputted forwardly of a front end face of the observation sleeve.

BRIEF DESCRIPTION OF THE DRAWINGS

FIG. 8 is a sectional view of a portion of a further modified otoscope according to the present invention.

DETAILED DESCRIPTION OF THE EMBODIMENTS

The present invention will now be described with reference to the drawings.

Figure 1:
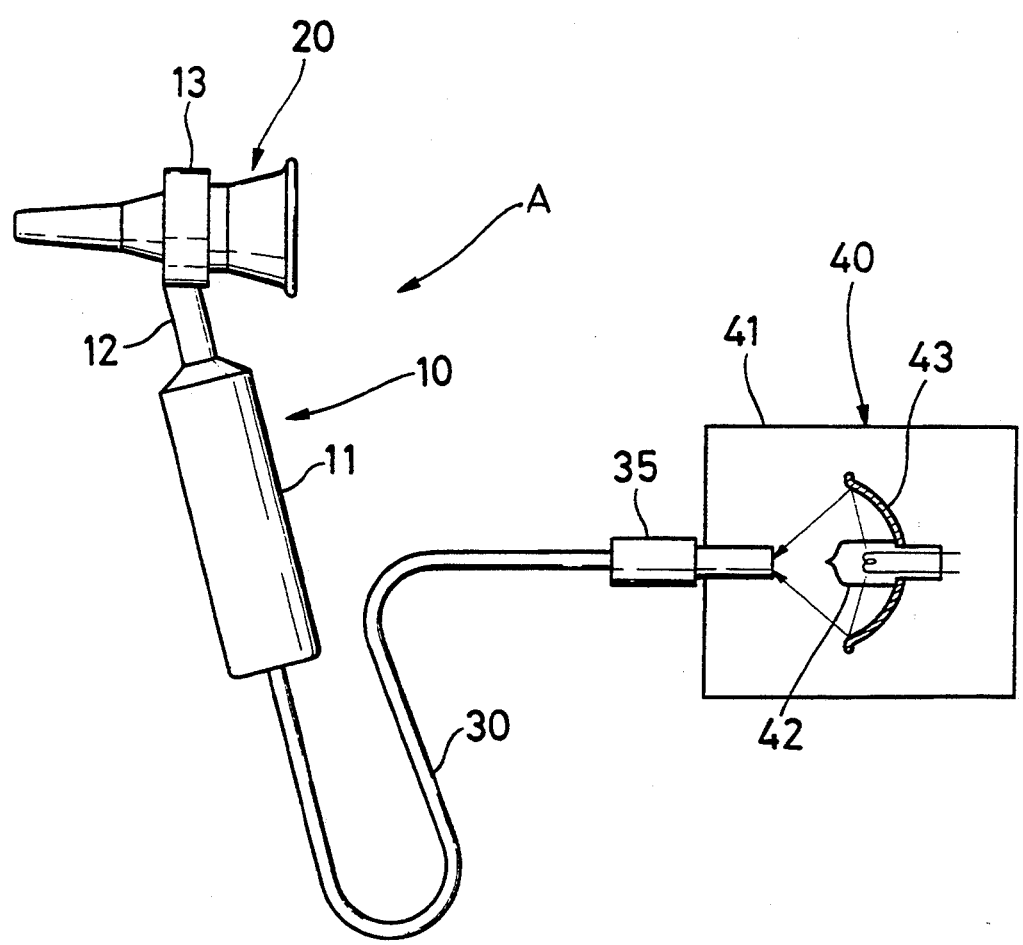
FIG. 1 is a schematic view showing an otoscope according to the present invention and a light source device.

FIGS. 1 to 4 show one embodiment of the present invention. As depicted in FIG. 1, an otoscope A comprises a body 10, and an observation sleeve 20 removably attached to this body 10.

Figure 2:
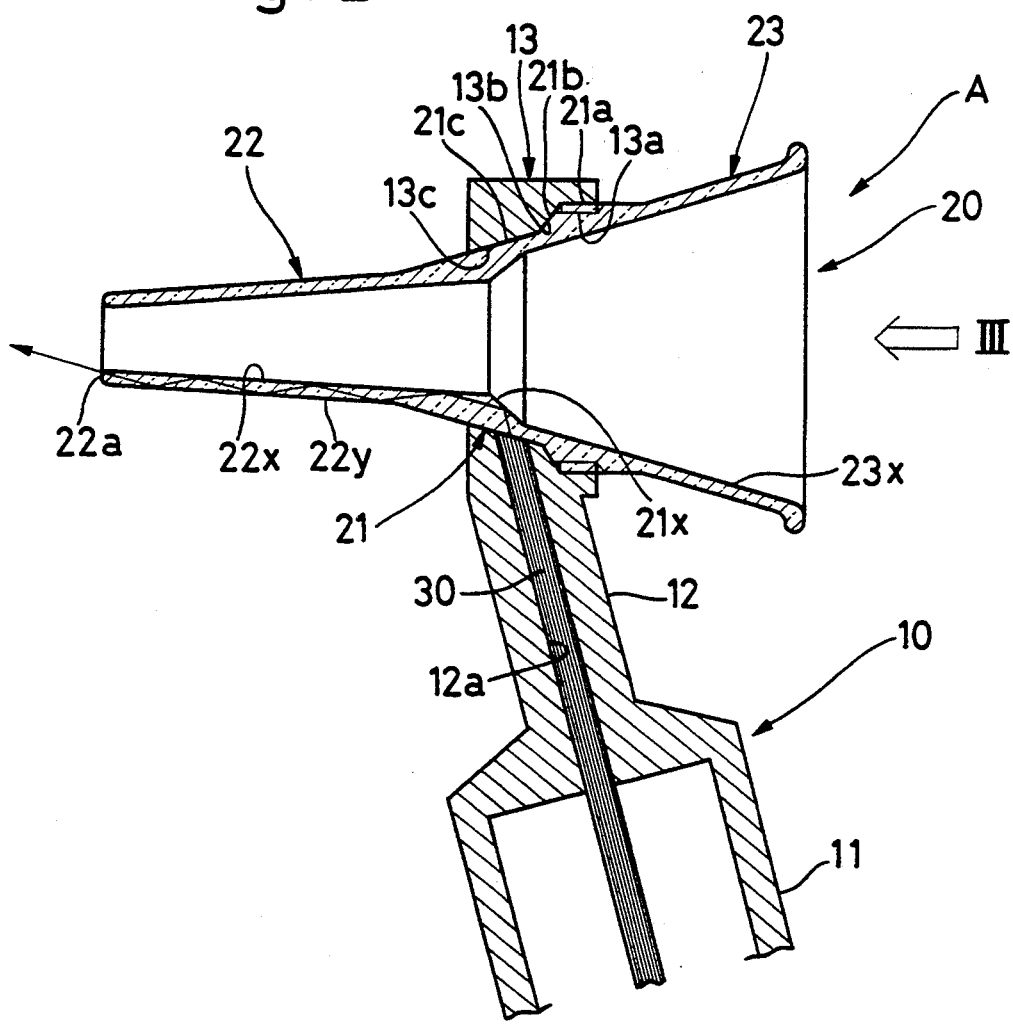
FIG. 2 is a sectional view of a portion of the otoscope of FIG. 1.
Figure 3:
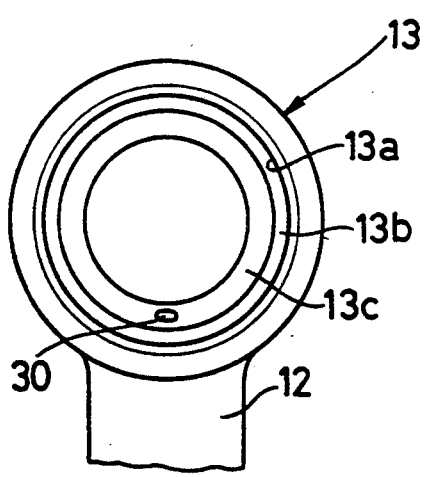
FIG. 3 is a front view of a portion of a body of the otoscope viewed in the direction of III of FIG. 2.

The body 10 comprises an elongated hollow grip portion 11, a neck portion 12 formed at a distal end of the grip portion 11 and extending longitudinally of the grip portion 11, and an annular support portion 13 formed at a distal end of the neck portion 12. As shown in FIG. 2, an inner periphery of the support portion 13 is provided, in order toward the left, with a female screw 13a, a comparatively steeply tapered surface 13b, and a comparatively gently tapered surface 13c.

The above observation sleeve 20 is made of a transparent material such as glass or resin, and has, as shown in FIG. 2, a frusto-conical configuration of a circular section. In other words, outside and inside diameters of the observation sleeve 20 are gradually reduced from the right-hand end of the observation sleeve 20 to the left-hand end thereof. An intermediate portion 21 of the observation sleeve 20 is provided as a portion to be mounted to the support portion 13 of the body 10 (hereinafter referred to as the "mount portion"). In the observation sleeve 20, a left-hand portion with reference to the mount portion 21 is referred to as a distal end portion 22, and a right-hand portion, as a basal end portion 23. An outer periphery of the mount portion 21 is provided, in order toward the left (i.e., toward the distal end of the observation sleeve 20), with a male screw 21a, a comparatively steeply tapered surface 21b, and a comparatively gently tapered surface 21c. The mount portion 21 of the observation sleeve 20 is inserted into the support portion 13 of the body 10 with the male screw 21a being threadedly engaged with the female screw 13a of the support portion 13. By threading the mount portion 21 of the observation sleeve 20 into the support portion 13 of the body 10 until the tapered surfaces 21b and 21c of the mount portion 21 are brought respectively into contact with the tapered surfaces 13b and 13c of the support portion 13, the observation sleeve 20 is removably attached to the support portion 13. Since the support portion 13 is in contact with the entire periphery of the mount portion 21 of the observation sleeve 20, the support for the observation sleeve 20 is stable. As shown in FIG. 1, since the support portion 13 is inclined longitudinally of the grip portion 11 as well as the neck portion 12, the basal end portion 23 of a larger diameter of the observation sleeve 20 forms a smaller angle than 90 degrees with respect to the longitudinal direction of the grip portion 11 as well as the neck portion 12, whereas the distal end 22 of a smaller diameter of the observation sleeve 20 forms a larger angle than 90 degrees with respect to the longitudinal direction of the grip portion 11 as well as the neck portion 12.

As shown in FIG. 1, the body 10 is connected to a light source device 40 through a light guide 30 formed of an optical fiber bundle covered with a soft resin tube.

As shown in FIG. 2, a receiving channel 12a is formed in the neck portion 12 of the body 10 and extends axially of the neck portion 12. This receiving channel 12a is open to the tapered surface 13c of the support portion 13. One end portion (light emission means) of the light guide 30 is extended through the basal end portion of the grip portion 11 of the body 10, and received and secured in the receiving channel 12a. One end face of the light guide 30 is coincident with one end of the receiving channel 12a, and faced with the tapered surface 21c of the mount portion 21 of the observation sleeve 20. As shown in FIG. 1, the other end portion of the light guide 30 is received and secured in a cylindrical rigid connector 35. This connector 35 is to be inserted into a housing 41 of the light source device 40. A lamp 42 and a concave mirror 43 are received in the light source device 40. Light from the lamp 42 is reflected by the concave mirror 43 in such a manner so as to converge at the other end face of the light guide 30. The light converged to the other end face of the light guide 30 is allowed to pass through the light guide 30, be emitted from the one end face of the light guide 30, and then be supplied to a peripheral wall of the observation sleeve 20.

As shown in FIG. 2, inner peripheries of the basal end portion 23, the mount portion 21, and the distal end portion 22 all of the observation sleeve 20 are provided respectively with tapered surfaces 23x, 21x, and 22x. Among these tapered surfaces, the tapered surface 21x has the largest cone angle, and the tapered surface 22x has the smallest cone angle. An outer periphery of the distal end portion 22 is provided with a tapered surface 22y having a cone angle equal to that of the tapered surface 22x of the inner periphery.

Figure 4:
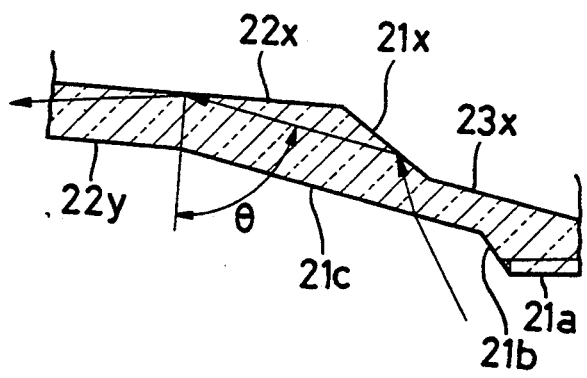
FIG. 4 is an enlarged sectional view of a portion of an observation sleeve showing a process of an illumination light proceeding through of a peripheral wall of the observation sleeve.

With the above construction, the physician holds the grip portion 11 of the body 10 by the hand and inserts the distal end portion 22 of the observation sleeve 20 into the patient's ear. As shown in FIGS. 2 and 4, an illumination light outputted from the one end of the light guide 30 is allowed to enter into the peripheral wall of the mount portion 21 through the tapered surface 21c of the outer periphery of the mount portion 21 of the observation sleeve 20, and then reflected by the tapered surface 21x of the inner periphery of the mount portion 21. Since this tapered surface 21x is steep, it totally reflects the illumination light from the light guide 30 and directs the illumination light forwardly of the observation sleeve 20. The illumination light reflected by the tapered surface 21x is passed through the peripheral wall of the distal end portion 22 of the observation sleeve 20 while being reflected by the tapered surfaces 22x and 22y of the outer and inner peripheries of the observation sleeve 20, and then irradiated into the ear canal from the distal end face 22a of the observation sleeve 20. More specifically, since an angle formed between an optical axis of the illumination light reflected by the tapered surface 21x and the axis of the observation sleeve 20 is small, an angle $\theta$ (FIG. 4) formed between the optical axis of the illumination light and normal lines of the tapered surfaces 22x and 22y becomes large, thereby ensuring the total reflection of the illumination light by the tapered surfaces 22x and 22y. In other words, the cone angle of the tapered surface 21x is determined taking into consideration a refractive factor of a material constituting the observation sleeve 20 and an angle of incidence of the illumination light to the tapered surface 21c of the outer periphery of the mount portion 21, so that the illumination light outputted from the light guide 30 would be totally reflected at the tapered surface 21x and so that the illumination light reflected here would be totally reflected by the tapered surfaces 22x and 22y. Since the illumination light is diverged circumferentially of the distal end portion 22 of the observation sleeve 20 when it is totally reflected by the tapered surfaces 22x and 22y, the illumination light is irradiated from the entire area of the distal end face 20a of the observation sleeve 20.

The physician can observe the ear canal by the illumination light output from the distal end face 22a of the observation sleeve 20. And various instruments are inserted, as needed, into the ear canal through the observation sleeve 20 in order to carry out a medical treatment. At that time, the observation sleeve 20 is soiled.

After completion of the medical treatment, the observation sleeve 20 is turned to remove the threaded engagement between the male screw 21a and the female screw 13a, and the observation sleeve 20 is detached from the support portion 13 so as to be disposed. Then, a new observation sleeve is attached to the support portion 13 for the next patient. In this way, the soiled observation sleeve 20 is not required to be used again, and there is an improvement in sanitation. Moreover, the observation sleeve 20 has a frusto-conical configuration of a circular section, and does not have the optical fiber bundle for conducting an illumination light and does not have the projection, unlike the prior art. Accordingly, the observation sleeve 20 is inexpensive to manufacture and disposable.

Several modified embodiments of the present invention will be described next. In the modified embodiments to follow, structure different from that of the preceding embodiment are described, and similar component parts are designated by similar reference numerals and description thereof is omitted.

Figure 5:
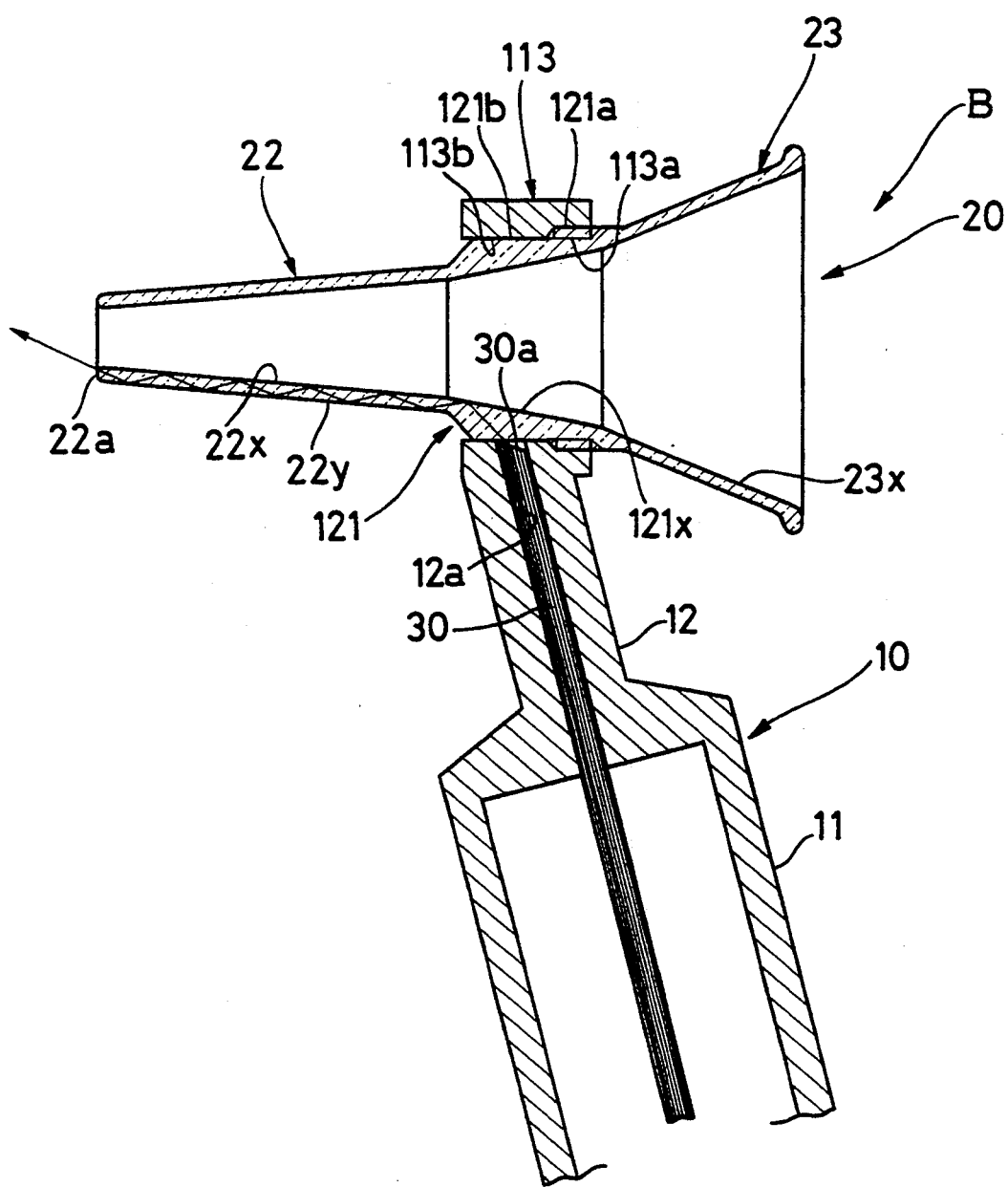
FIG. 5 is a sectional view of a portion of a modified otoscope according to the present invention.

In a modified otoscope B of FIG. 5, an outer periphery of a support portion 113 of a body 10 is provided with a female screw 113a and a cylindrical surface 113b. An outer periphery of a mount portion 121 of an observation sleeve 20 is provided with a male screw 121a adapted to engage with the female screw 113a and a cylindrical surface 121b adapted to contact the cylindrical surface 113b. A tapered surface 121x of an inner periphery of the mount portion 121 is more gentle than the tapered surface 21x of the above embodiment. However, one end face 30a of a light guide 30 is greatly inclined with respect to an axis of the light guide 30 so that an illumination light to be outputted from this one end face 30a would be inclined closer to the axis of the observation sleeve 20. Due to this arrangement, the illumination light output from the light guide 30 is totally reflected by the tapered surface 121x and then, the illumination light is totally reflected by tapered surfaces 22x and 22y of a distal end portion 22 of the observation sleeve 20.

Figure 6:
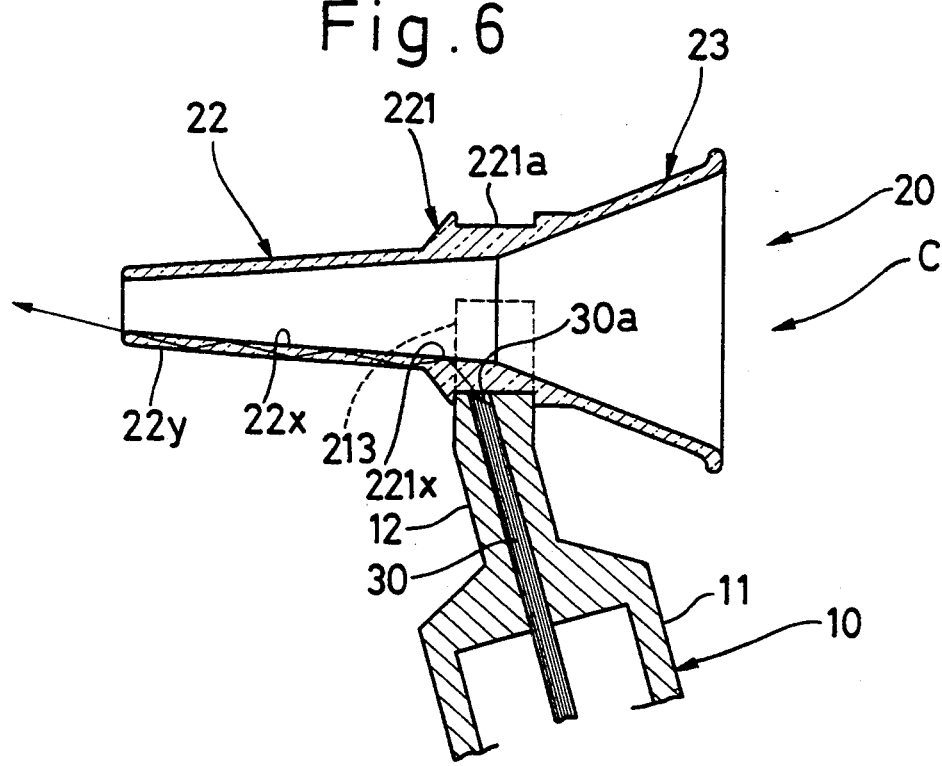
FIG. 6 is a sectional view of a portion of another modified otoscope according to the present invention.
Figure 7:
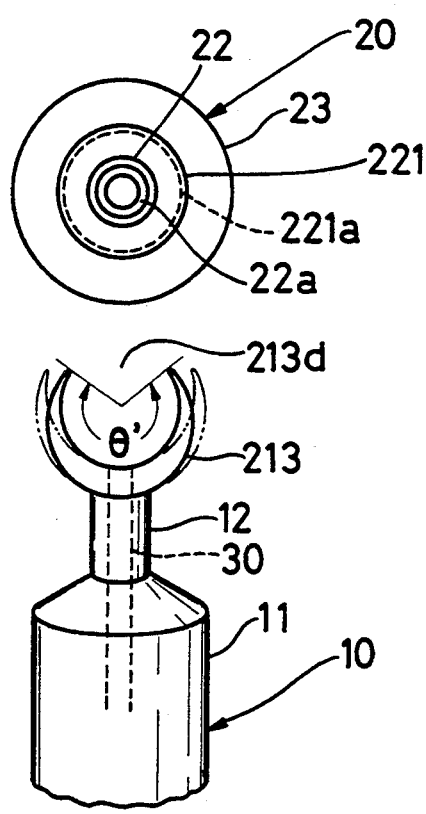
FIG. 7 is an exploded front view of the otoscope of FIG. 6.

In another modified otoscope C of FIGS. 6 and 7, an inner peripheral surface of a support portion 213 is disposed on an imaginary circle, occupying an angle larger than 180 degrees θ. An annular recess 221a is formed in an outer periphery of a mount portion 221 of an observation sleeve 20. The diameter of this recess 221a is equal to or slightly larger than the inside diameter of the support portion 213. By pushing the mount portion 221 of the observation sleeve 20 into a space 213d formed between opposite ends of the support portion 213, the support portion 213 is snap fit in the recess 221a, and as a result, the observation sleeve 20 is removably attached to the support portion 213. In order achieve this snap fitting, at least the support portion 213 and preferably, a whole body 10 is made of elastically deformable resin. Alternatively, there may be an arrangement in which the support member 213 is rigid, and the observation sleeve 20 is made of elastic resin.

In the otoscope C shown in FIGS. 6 and 7, an inner periphery of the mount portion 221 of the observation sleeve 20 is provided with a gently tapered surface 221x having a cone angle equal to that of the tapered surface 22x of an inner periphery of a distal end portion 22. In this embodiment, since one end face 30a of a light guide 30 is greatly inclined enough with respect to an axis of the light guide 30, an illumination light output from this one end face 30a is totally reflected by the tapered surface 221x of the mount portion 221 and then totally reflected by the tapered surfaces 22x and 22y of the distal end portion 22.

In a further modified otoscope D of FIG. 8, a lamp 330 is used as light emission means. The lamp 330 is received in a receiving channel 12a formed in a neck portion 12. A grip portion 11 of a body 10 contains batteries 340 and is connected to the lamp 330.

The present invention is not limited to the above embodiments, and various modifications can be made without departing from the scope of the invention. For example, in the observation sleeve 20 of FIG. 2, a reflection layer such as a metal plated layer may be formed on the tapered surfaces 21x, 22x and 22y reflecting the illumination light. The present invention is likewise applicable to other medical observation apparatuses than the otoscope.

What is claimed is:

1. A medical observation instrument, said instrument comprising:
    (a) a body including a grip portion, a support portion disposed at a distal end of said grip portion, said support portion having a circular arcuate portion, a receiving hole formed in a portion of an inner peripheral surface of said circular arcuate portion corresponding to said grip portion, and tapered support surface, said tapered support surfaces comprising a steeply tapered support surface and a gently tapered support surface;
    (b) an observation sleeve removably attached to said body and extending in a direction intersecting a longitudinal direction of said grip portion of said body, said observation sleeve being made of a transparent material, said observation sleeve including a mount portion having a circular section received in and removably attached to said support portion of said body, and a distal end portion having a circular section that extends forward from said mount portion, said mount portion having a tapered surface serving as a first reflecting surface at an inner peripheral surface of said mount portion, said distal end portion having tapered surfaces serving as second and third reflecting surfaces, respectively, at inner and outer peripheral surfaces of said distal end portion, a taper angle of said first reflecting surface being greater than those of said second and third reflecting surfaces; and
    (c) light emission means for supplying an illumination light to said observation sleeve, said light emission means received in said receiving hole of said body and facing an outer peripheral surface of said mount portion of said observation sleeve, said illumination light from said light emission means being emitted so that said illumination light is incident on said outer peripheral surface of said mount portion of said observation sleeve, being reflected by said first reflecting surface of said mount portion toward said distal end of said observation sleeve, passing through a peripheral wall of said distal end portion while being reflected by said second and third reflecting surfaces of said distal end portion, and then being outputted forward from a front end face of said observation sleeve.

2. A medical observation instrument as claimed in claim 1, wherein said mount portion of said observation sleeve has a tapered surface at an inner peripheral surface, said tapered surface reflecting said illumination light entering a peripheral wall of said mount portion from said light emission means so that said illumination light is directed toward said distal end of said observation sleeve.

3. A medical observation instrument as claimed in claim 2, wherein said inner and outer peripheral surfaces of said distal end portion of said observation sleeve have tapered surfaces, and a cone angle of said mount portion is larger than said tapered surfaces of said inner and outer peripheral surfaces of said distal end portion.

4. A medical observation instrument as claimed in claim 1, wherein said distal end of said grip portion of said body has a neck portion having a smaller cross section than said grip portion and extending longitudinally from said grip portion, said neck portion disposed at said distal end of said grip portion with said support portion.

5. A medical observation instrument, said instrument comprising:
   (a) a body including a grip portion, a support portion disposed at a distal end of said grip portion, said support portion having a circular arcuate portion and a receiving hole formed in a portion of an inner peripheral surface of said circular arcuate portion corresponding to said grip portion;
   (b) an observation sleeve removably attached to said body and extending in a direction intersecting a longitudinal direction of said grip portion of said body, said observation sleeve being made of a transparent material, said observation sleeve including a mount portion having a circular section received in and removably attached to said support portion of said body, and a distal end portion having a circular section that extends forward from said mount portion; and
   (c) light emission means for supplying an illumination light to said observation sleeve, said light emission means received in said receiving hole of said body and facing an outer peripheral surface of said mount portion of said observation sleeve, said illumination light from said light emission means being emitted so that said illumination light is incident on said outer peripheral surface of said mount portion of said observation sleeve, being reflected by an inner peripheral surface of said mount portion, passing through a peripheral wall of said distal end portion while being reflected by inner and outer peripheral surfaces of said distal end portion, and then being outputted forward from a front end face of said observation sleeve,
   wherein said support portion of said body has an annular shape, a female screw formed in an inner periphery of said support portion, and a male screw formed on an outer periphery of said mount portion of said observation sleeve so as to be threadedly engaged with said female screw and thereby prevent rotation of the observation sleeve.

6. A medical observation instrument, said instrument comprising:
   (a) a body including a grip portion, a support portion disposed at a distal end of said grip portion, said support portion having a circular arcuate portion and a receiving hole formed in a portion of an inner peripheral surface of said circular arcuate portion corresponding to said grip portion;
   (b) an observation sleeve removably attached to said body and extending in a direction intersecting a longitudinal direction of said grip portion of said body, said observation sleeve being made of a transparent material, said observation sleeve including a mount portion having a circular section received in and removably attached to said support portion of said body, and a distal end portion having a circular section that extends forward from said mount portion; and
   (c) light emission means for supplying an illumination light to said observation sleeve, said light emission means received in said receiving hole of said body and facing an outer peripheral surface of said mount portion of said observation sleeve, said illumination light from said light emission means being emitted so that said illumination light is incident on said outer peripheral surface of said mount portion of said observation sleeve, being reflected by an inner peripheral surface of said mount portion, passing through a peripheral wall of said distal end portion while being reflected by inner and outer peripheral surfaces of said distal end portion, and then being outputted forward from a front end face of said observation sleeve,
   wherein said support portion of said body has an annular shade, a female screw formed in an inner periphery of said support portion, and a male screw formed on an outer periphery of said mount portion of said observation sleeve so as to be threadedly engaged with said female screw, and said inner periphery of said support portion has a tapered surface located forwardly of said female screw and said outer periphery of said mount portion of said observation sleeve has a tapered surface for contacting said tapered surface of said inner periphery of said support portion.

7. A medical observation instrument, said instrument comprising:
   (a) a body including a grip portion, a support portion disposed at a distal end of said grip portion, said support portion having a circular arcuate portion and a receiving hole formed in a portion of an inner peripheral surface of said circular arcuate portion corresponding to said grip portion;
   (b) an observation sleeve removably attached to said body and extending in a direction intersecting a longitudinal direction of said grip portion of said body, said observation sleeve being made of a transparent material, said observation sleeve including a mount portion having a circular section received in and removably attached to said support portion of said body, and a distal end portion having a circular section that extends forward from said mount portion; and
   (c) light emission means for supplying an illumination light to said observation sleeve, said light emission means received in said receiving hole of said body and facing an outer peripheral surface of said mount portion of said observation sleeve, said illumination light from said light emission means being emitted so that said illumination light is incident on said outer peripheral surface of said mount portion of said observation sleeve, being reflected by an inner peripheral surface of said mount portion, passing through a peripheral wall of said distal end portion while being reflected by inner and outer peripheral surfaces of said distal end portion, and then being outputted forward from a front end face of said observation sleeve, wherein said circular arcuate portion of said support portion has opposite ends spaced away from each other in a circumferential direction of said circular arcuate portion to form an insert space therebetween, and an annular recess formed in an outer periphery of said mount portion of said observation sleeve, said circular arcuate portion of said support portion and said annular recess portion snap fit together when said observation sleeve is inserted into said insertion space of said support portion.

8. A medical observation instrument, said instrument comprising:
  (a) a body including a grip portion, a support portion disposed at a distal end of said grip portion, said support portion having a circular arcuate portion and a receiving hole formed in a portion of an inner peripheral surface of said circular arcuate portion corresponding to said grip portion;
  (b) an observation sleeve removably attached to said body and extending in a direction intersecting a longitudinal direction of said grip portion of said body, said observation sleeve being made of a transparent material, said observation sleeve including a mount portion having a circular section received in and removably attached to said support portion of said body, and a distal end portion having a circular section that extends forward from said mount portion; and
  (c) light emission means for supplying an illumination light to said observation sleeve, said light emission means received in said receiving hole of said body and facing an outer peripheral surface of said mount portion of said observation sleeve, said illumination light from said light emission means being emitted so that said illumination light is incident on said outer peripheral surface of said mount portion of said observation sleeve, being reflected by an inner peripheral surface of said mount portion, passing through a peripheral wall of said distal end portion while being reflected by inner and outer peripheral surfaces of said distal end portion, and then being outputted forward from a front end face of said observation sleeve, wherein said light emission means comprises an end portion of a light guide having an optical fiber bundle, and an end face of said light guide is inclined with respect to an axis of said light guide such that an angle formed between an optical axis of said illumination light output from said end face of said light guide and an axis of said observation sleeve is smaller than an angle formed between the axis of said light guide and the axis of said observation sleeve.

9. A medical observation instrument, said instrument comprising:
  (a) a body including a grip portion, a support portion disposed at a distal end of said grip portion, said support portion having a circular arcuate portion and a receiving hole formed in a portion of an inner peripheral surface of said circular arcuate portion corresponding to said grip portion;
  (b) an observation sleeve removably attached to said body and extending in a direction intersecting a longitudinal direction of said grip portion of said body, said observation sleeve being made of a transparent material, said observation sleeve including a mount portion having a circular section received in and removably attached to said support portion of said body, and a distal end portion having a circular section that extends forward from said mount portion; and
  (c) light emission means for supplying an illumination light to said observation sleeve, said light emission means received in said receiving hole of said body and facing an outer peripheral surface of said mount portion of said observation sleeve, said illumination light from said light emission means being emitted so that said illumination light is incident on said outer peripheral surface of said mount portion of said observation sleeve, being reflected by an inner peripheral surface of said mount portion, passing through a peripheral wall of said distal end portion while being reflected by inner and outer peripheral surfaces of said distal end portion, and then being outputted forward from a front end face of said observation sleeve, wherein said inner and outer peripheral surfaces of said observation sleeve are coated with reflecting materials for reflecting said illumination light.

* * * * *